US00PP18778P2

(12) United States Plant Patent
Bradford

(10) Patent No.: US PP18,778 P2
(45) Date of Patent: Apr. 29, 2008

(54) NECTARINE TREE NAMED 'MAJESTIC PEARL'

(50) Latin Name: *Prunus persica*
Varietal Denomination: Majestic Pearl

(76) Inventor: Lowell Glen Bradford, 10237 E. Mariposa Way, Le Grand, CA (US) 95333

( * ) Notice: Subject to any disclaimer, the term of this patent is extended or adjusted under 35 U.S.C. 154(b) by 0 days.

(21) Appl. No.: 11/637,879

(22) Filed: Dec. 13, 2006

(51) Int. Cl.
*A01H 5/00* (2006.01)

(52) U.S. Cl. ..... Plt./188
(58) Field of Classification Search ..... Plt./188
See application file for complete search history.

(56) References Cited

U.S. PATENT DOCUMENTS

PP7,507 P 4/1991 Bradford
PP9,359 P 11/1995 Bradford

*Primary Examiner*—Kent Bell

(57) ABSTRACT

The present invention relates to a new and distinct variety of nectarine tree, *Prunus persica,* broadly characterized by a large size, vigorous, hardy, self-fertile, productive and regular bearing tree. The fruit matures under the ecological conditions described in late July, with first picking on Jul. 23, 2006. The fruit is uniformly large in size, sub-acidic and sweet in flavor, globose in shape, clingstone in type, very firm in texture, white in flesh color, and mostly red in skin color.

1 Drawing Sheet

Figure 1A:
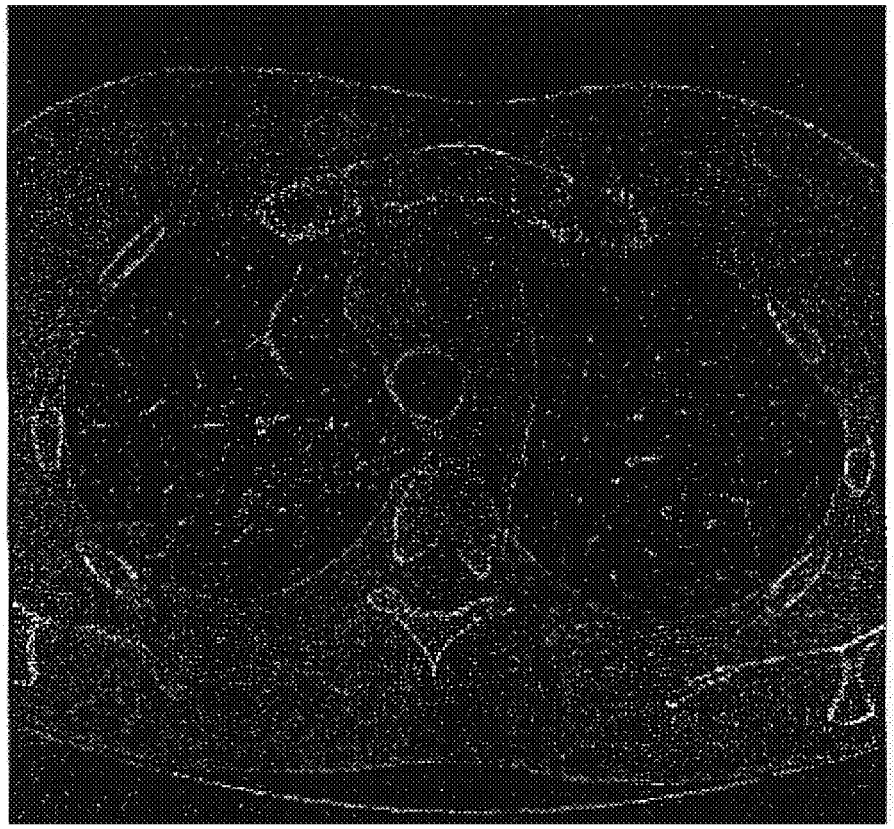
Figure 1B:
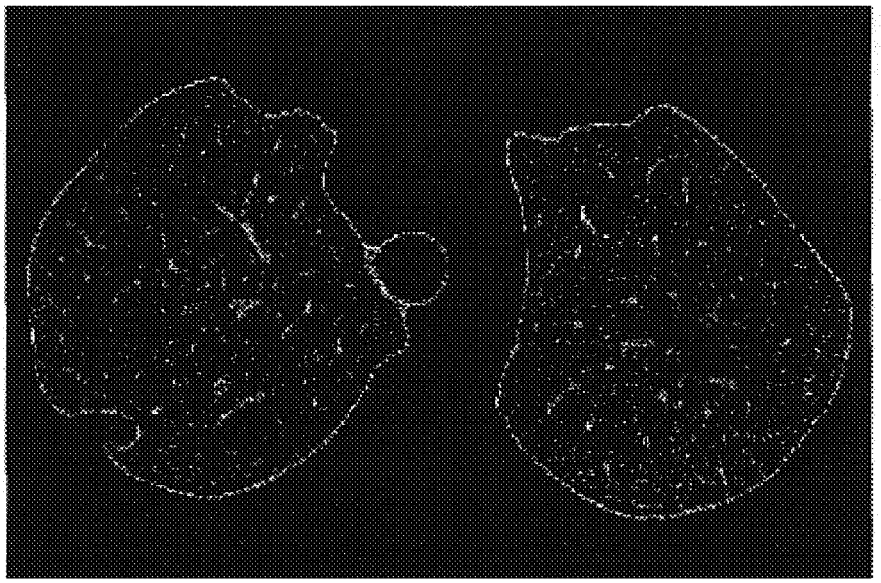

Botanical classification: *Prunus persica.*
Variety denomination: 'MAJESTIC PEARL'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits, usually to capture recessive traits. The present invention relates to a new and distinct variety of nectarine tree, which has been denominated varietally as 'MAJESTIC PEARL'.

During the spring of 1998 I gathered fruit from an unpatented nectarine tree in my experimental orchard located near Le Grand, Calif., in Merced County (San Joaquin Valley) that had been designated as "5P452". This particular nectarine tree was itself a first generation cross using 'Spring Bright' (U.S. Plant Pat. No. 7,507) yellow flesh nectarine as the selected seed parent and an unnamed white flesh nectarine (unpatented) as the selected pollen parent. The seeds from this fruit were removed, cracked, stratified, germinated, and grown as seedlings on their own root in my greenhouse as a group labeled "5P452 (OP)". Upon reaching dormancy that fall I transplanted these seedlings to a cultivated area in the experimental orchard described above. During the fruit evaluation season of 2001 I selected the present variety as a single tree from the group of "5P452 (OP)" seedlings described above. Subsequent to origination of the present variety of nectarine tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to its seed grandparent, 'Spring Bright' (U.S. Plant Pat. No. 7,507) nectarine by producing nectarines that are firm, globose in shape, and almost full red in skin color, but is quite distinct by producing fruit that is white instead of yellow in flesh color, sub-acidic instead of acidic in flavor, and by maturing about thirty days later.

The present variety is most similar to 'Bright Pearl' (U.S. Plant Pat. No. 9,359) nectarine by producing nectarines that are nearly globose in shape, firm in texture, white in flesh color, and mostly red in skin color, but is distinguished therefrom by being more productive, by requiring a lower amount of chilling, by having reniform instead of globose leaf glands, and by producing fruit that is larger in size.

SUMMARY OF VARIETY

In summary, the present variety is characterized by a large size, vigorous, hardy, self-fertile, productive and regular bearing tree. The fruit matures under the ecological conditions described in late July, with first picking on Jul. 23, 2006. The fruit is uniformly large in size, sub-acidic and sweet in flavor, globose in shape, clingstone in type, very firm in texture, white in flesh color, and mostly red in skin color.

DRAWING

The accompanying photograph consists of four whole fruits positioned to display the characteristics of the skin color and form, one fruit divided transversely to the suture plane to reveal the flesh and stone, two insets to reveal buds and blossoms in various stages, various leaves, and a typical tip shoot.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of firm ripe on Jul. 27, 2006, on the original tree during its eighth growing season. All major color code designations are by reference to the Inter-Society Color Council, National Bureau of Standards. Common color names are also used occasionally.

Parentage

Parentage: An open pollinated seedling of '5P452' (Unpatented) Nectarine.

Tree

Size: Large, reaching and maintaining a height of 11' [3.35 m.] and a spread of 11' [3.35 m.] after eight growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commercial rootstock for production purposes.

Growth: Spreading and dense.

Form: Vase formed.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive, thinning necessary.

Fertility: Self-fertile.

Bearing: Regular bearer with no alternate bearing yet observed.

Approximate chilling requirement: 575 hours.

Trunk:

*Size.*—Medium, reaching a maximum diameter of 5¾" [146 mm.] after the eighth growing season.

*Texture.*—Shaggy.

*Bark color.*—A Brownish gray [64. brGy] and Deep brown [56. deep Br] variegation with Light orange yellow [70. l.OY] crevices present.

*Lenticels.*—Approximate Number Per Square Inch: 8. Color: Moderate orange yellow [71. m.OY]. Typical Size: ⅛" [3.2 mm.] to 7/16" [11.1 mm.]. Shape: Eye-shaped to elongated.

Branches:

*Size.*—Diameter of limb is 3¼" [83 mm.] measured 12" above the crotch, 2¼" [57 mm.] measured 12" above the first fork.

*Texture.*—Smooth on first and second year wood, increasing roughness with age.

*Color.*—1st Year Wood Topside: Grayish red [19. gyR]. 1st Year Wood Underside: Brilliant yellow green [116. brill.YG]. Older Wood: Deep yellowish brown [75. deep yBr].

*Lenticels.*—Number Per Square Inch: More than 50 on second year wood. Color: Light yellowish brown [76. l.yBr]. Typical size: 1/64" [0.4 mm.] to ⅛" [3.2 mm.] on second year wood. Shape: Elongated.

Leaves:

*Size.*—Large. Average Length: 5 13/16" [148 mm.]. Average width: 1⅞" [48 mm.].

*Arrangement.*—Alternate.

*Thickness.*—Medium.

*Form.*—Elliptical.

*Apex.*—Acuminate.

*Base.*—Acute, with an average base angle of 65 to 75 degrees.

*Surface.*—Smooth.

*Color.*—Dorsal Surface: Deep yellow green [118. deep YG]. Ventral Surface: Moderate yellow green [120. m.YG].

*Margin.*—Finely serrate.

*Venation.*—Pinnately net veined.

*Petiole.*—Average Length: 7/16" [11.1 mm.]. Average Thickness: 1/16" [1.6 mm.]. Color: Brilliant yellow green [116. brill.YG].

*Stipules.*—Number: 2 per leaf, up to 6 per growing tip. Average Length: ¼" [6.4 mm.]. Color: Brilliant yellow green [11.6. brill.YG] turning Strong reddish brown [40. s.rBr] with maturity.

*Glands.*—Number: 2 to 5 per leaf. Position: Alternately positioned on both the petiole and the base of blade. Size: Medium to large. Form: Reniform. Color: Strong yellow green [117. s.YG] on younger leaves turning Moderate reddish brown [43. m.rBr] in the center with maturity.

*Leaf buds.*—Medium in size, pointed.

Flower buds:

*Hardiness.*—Hardy, with respect to central California winters.

*Diameter.*—Typically ⅜" [9.5 mm.] 1 week before bloom.

*Length.*—Typically 11/16" [17.5 mm.] 1 week before bloom.

*Form.*—Not appressed.

*Surface.*—Pubescent.

*Color.*—Light purplish pink [249. l.pPk].

Flowers: Perfect, complete, perigynous, usually a single pistil, typically thirty or more stamens, five sepal and petal locations alternately positioned.

*Type.*—Showy, very large.

*Average flower diameter.*—2 1/16" [52.4 mm.].

*Number of petals.*—Usually five, a few with extra petal fragments and a few double blossoms.

*Petal shape.*—Circular to oval.

*Petal Margin.*—Somewhat wavy.

*Average petal diameter.*—13/16" [20.6 mm.].

*Average petal length.*—13/16" [20.6 mm.].

*Petal apex.*—Rounded.

*Petal base.*—Rounded to somewhat truncate.

*Petal color.*—Pale pink [7. p.Pk] toward the apex light. purplish pink [249. l.pPk] toward the base.

*Anther color.*—Dark red [16. d.R] over a Light yellow [86. l.Y] center at bloom onset.

*Stigma color.*—Light greenish yellow [101. l.gY].

*Sepal color.*—Dark purplish red [259. d.pR].

*Sepal length.*—5/16" [7.9 mm.].

*Sepal width.*—¼" [6.4 mm.].

*Average pistil length.*—13/16" [20.6 mm.].

*Average stamen length.*—⅝" [15.9 mm.].

*Fragrance.*—Moderate.

*Blooming period.*—Medium, approximately with 'Spring Bright' (U.S. Plant Pat. No. 7,507) nectarine.

*Onset of bloom.*—One percent on Feb. 23, 2006.

*Date of full bloom.*—Mar. 8, 2006.

*Duration of bloom.*—One to two weeks, dependent on ambient temperature.

*Number per cluster.*—1 to 3 with single flowers most common.

FRUIT

Maturity when described: Firm ripe, Jul. 27, 2006.
Date of first picking: Jul. 23, 2006.
Date of last picking: Aug. 3, 2006.
Size: Uniform, large.
*Average diameter axially.*—3¼" [82.6 mm.].
*Average diameter across cheek plane.*—3⅛" [79.4 mm.].
*Average diameter across suture plane.*—3⅛" [79.4 mm.].
*Typical weight.*—8.1 ounces [230 grams].
Form: Uniform, symmetrical, globose to slightly oblong.
*Longitudinal section form.*—Round to oval.
*Axial view form.*—Round.
Suture: A sharp groove in the stem cavity, a shallow trough along the side, and a sharp groove toward the apex ending in a slight depression just beyond the pistil point.
Ventral surface: Rounded, lipped throughout on both sides.
Lips: Mostly equal.
Cavity: Flaring, circular to slightly elongated in the suture plane, suture showing on one side, Pale greenish yellow [104. p.gY] stem markings typical.
*Depth.*—9/16 [14.3 mm.].
*Breadth.*—1¼" [31.8 mm.].
Base: Rounded to truncate.
Apex: Rounded, somewhat cordate if viewed parallel to the suture.
Pistil point: Apical, short, 1/32" [0.8 mm.] typical length, depressed within the suture.
Stem: Medium.
*Average length.*—⅜" [9.5 mm.].
*Average width.*—3/16" [4.8 mm.].
Skin:
*Thickness.*—Medium.
*Surface.*—Smooth.
*Tenacity.*—Tenacious to flesh.
*Astringency.*—Non-astringent.
*Tendency to crack.*—None observed.
*Color.*—Very deep red [14. v.deep R] over a Moderate red [15. m.R] background, a small amount of Pale greenish yellow [104. p.gY] area where sun protected, and moderate Light orange yellow [70. l.OY] freckling toward the apex.
Flesh:
*Color.*—Greenish white [153. gWhite] with Very red [11. v.R] streaking next to the stone.
*Surface of pit cavity.*—Strong red [12. s.R] fibers breaking when twisted from the stone.
*Amygdalin.*—Scarce.
*Juice.*—Moderate.
*Texture.*—Firm, crisp, melting.
*Fibers.*—Abundant, fine.
*Ripens.*—Slightly earlier toward the apex.
*Flavor.*—Sub-acid and sweet, typically 18 brix.
*Aroma.*—Moderate.
*Eating quality.*—Excellent.

STONE

Type: Clingstone.
Form: Oval.
Hilum: Oval.
Base: Straight.
Apex: Acuminate, with an average tip length of 1/16" [1.6 mm.] and an average tip angle of 45 degrees.
Sides: Equal.
Surface: Irregularly furrowed near the apex and along the vertical edge, pitted from base to above center.
Ridges: Jagged.
External color of stone: Deep yellowish brown [75. deep yBr] when freshly removed.
Pit wall color when cracked: Light yellowish brown [76. l.yBr].
Cavity surface color: Dark orange yellow [72. d.OY].
Average pit wall thickness: ¼" [6.4 mm.].
Average width: 1 1/16" [27 mm.].
Average length: 1⅝" [41.3 mm.].
Average breadth: ¾" [19.1 mm.].
Tendency to split: Slight.
Kernel:
*Form.*—Oval.
*Skin color.*—Deep orange yellow [69. deep OY].
*Pellicle color.*—Moderate yellowish brown [77. m.yBr].
*Vein color.*—Strong yellowish brown [74. s.yBr].
*Taste.*—Bitter.
*Viable.*—Yes.
*Average width.*—7/16" [11.1 mm.].
*Average length.*—13/16" [20.6 mm.].
*Amygdalin.*—Abundant.

USE

Market: Fresh market and long distance shipping.
Keeping quality: Good, fruit quality observed to remain in good condition after 21 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of nectarine tree, substantially as illustrated and described, that is most similar to 'Bright Pearl' [U.S. Plant Pat. No. 9,359] nectarine by producing nectarines that are nearly globose in shape, firm in texture, white in flesh color, and mostly red in skin color, but is distinguished therefrom by being more productive, by requiring a lower amount of chilling, by having the reniform instead of globose leaf glands, and by producing fruit that is larger in size.

* * * * *